United States Patent [19]
Takahashi

[11] 3,958,945
[45] May 25, 1976

[54] SPARGING DEVICE

[75] Inventor: Yoshihiro Takahashi, San Francisco, Calif.

[73] Assignee: Envirotech Corporation, Menlo Park, Calif.

[22] Filed: Oct. 4, 1974

[21] Appl. No.: 511,970

[52] U.S. Cl. ............................ 23/259; 23/230 M; 23/230 PC; 23/253 PC; 23/253 R; 55/196; 137/210; 137/266; 261/122; 261/123

[51] Int. Cl.² .................. C02D 1/00; G01N 33/18; B01L 3/00

[58] Field of Search .......... 23/230 PC, 259, 253 PC, 23/252 R, 230 M, 253 R; 261/122, 22, 123, 124, 126, 125; 55/93, 196, 44, 47; 137/210, 266

[56] References Cited
UNITED STATES PATENTS

| | | | |
|---|---|---|---|
| 2,718,275 | 9/1955 | Banks | 55/93 |
| 2,935,057 | 5/1960 | Perlewitz | 137/266 |
| 3,397,731 | 8/1968 | Gravis et al. | 261/124 |
| 3,506,484 | 4/1970 | Domsa | 261/124 |
| 3,607,071 | 9/1971 | Colonia et al. | 23/230 PC |

*Primary Examiner*—Morris O. Wolk
*Assistant Examiner*—Dale Lovercheck
*Attorney, Agent, or Firm*—Robert E. Krebs; Thomas S. MacDonald

[57] ABSTRACT

A device for sparging carbon dioxide from an acidified aqueous stream for use in a system for quantitatively determining the organic carbon content of the stream has a body with vertically extending cavities formed therethrough and passageways which connect the cavities in series so that the aqueous stream travels the length of a cavity before passing into the next. Dispersion tubes are mounted in the cavities for dispersing fine bubbles of sparging gas into the aqueous stream. The gas and carbon dioxide which has evolved from the aqueous stream is collected and discharged through the cavities.

2 Claims, 3 Drawing Figures

SPARGING DEVICE

BACKGROUND OF THE INVENTION

1. Field of the Invention

This invention relates generally to an improved system for automatically analyzing liquid to determine its organic carbon content.

2. State of the Art

It is often desirable to determine the concentration of organic materials in liquid or semi-liquid streams. For instance, in wastewater treatment systems it is quite desirable to determine organic loading of plant effluent in order to avoid contamination and pollution of the natural bodies which receive such effluent. For industrial process streams, it also is often desirable to make determinations of organic loading.

Dissolved or suspended solid matter in aqueous streams can be generally classified as either of an organic or inorganic nature. Elemental carbon is always present in organic substances but is not necessarily present in inorganic materials. Since techniques for quantitatively determining the total carbon content of a sample are well-known, such techniques can be used to measure organic loading if inorganic carbon is eliminated prior to analysis. U.S. Pat. No. 3,607,071 teaches a continuous system for eliminating inorganic carbonaceous materials from an aqueous stream and then quantitatively determining the organic carbon content of the residual.

OBJECTS OF THE INVENTION

An object of the invention is to provide improved ways and means for continuously analyzing a liquid or semi-liquid stream to determine its organic carbon content.

A more specific object is to provide ways and means for continuously and immediately eliminating inorganic carbon compounds from an aqueous stream in conjunction with the analysis of the stream to determine organic loading.

An even more specific object is to provide an improved device for sparging carbon dioxide from an acidified aqueous stream for use in a system for quantitatively determining the organic carbon content of the stream.

BRIEF DESCRIPTION OF THE DRAWINGS

Further objects and advantages of the present invention can be readily ascertained by reference to the following description and appended drawings, which are offered by way of illustration only and not in limitation of the invention whose scope is defined in the appended claims and by equivalents to the structure, materials and acts recited therein. In the drawings:

DETAILED DESCRIPTION OF THE PREFERRED EMBODIMENT

The analysis system which is described hereinafter particularly well-suited for use in evaluating the organic loading of aqueous streams in water, wastewater, and sewage treatment operations wherein typically the most quantitatively significant inorganic carbonaceous substances are carbonate and bicarbonate salts such as sodium carbonate, ammonium bicarbonate and calcium carbonate. The prior art teaches that such inorganic carbonate and bicarbonate salts can be removed from an aqueous stream by acidification and sparging. More particularly, it is known that acid added to polluted water will react with inorganic carbonates and bicarbonate salts to form non-carbonate salts and carbon dioxide, the latter which can be removed from the water in a counter-current sparge column. Typically, hydrochloric acid is utilized for acidification but a number of other acids, such as nitric and phosphoric, could be employed. The following reaction, representative of an acidification step generally, occurs when hydrochloric acid is added to a sample containing calcium carbonate salts:

$$CaCO_3 + 2HCl \rightarrow CaCl_2 + H_2O + CO_2.$$

At least some of the carbon dioxide produced in the above reaction is stably hydrated or solvated in the aqueous phase. In order that subsequent quantitative analysis reflect only the presence of organic carbon, the carbon dioxide must be purged from the liquid. Improved ways and means will be described hereinafter for accomplishing such a purge on a continuous and immediate basis without excessive mixing.

Figure 1:
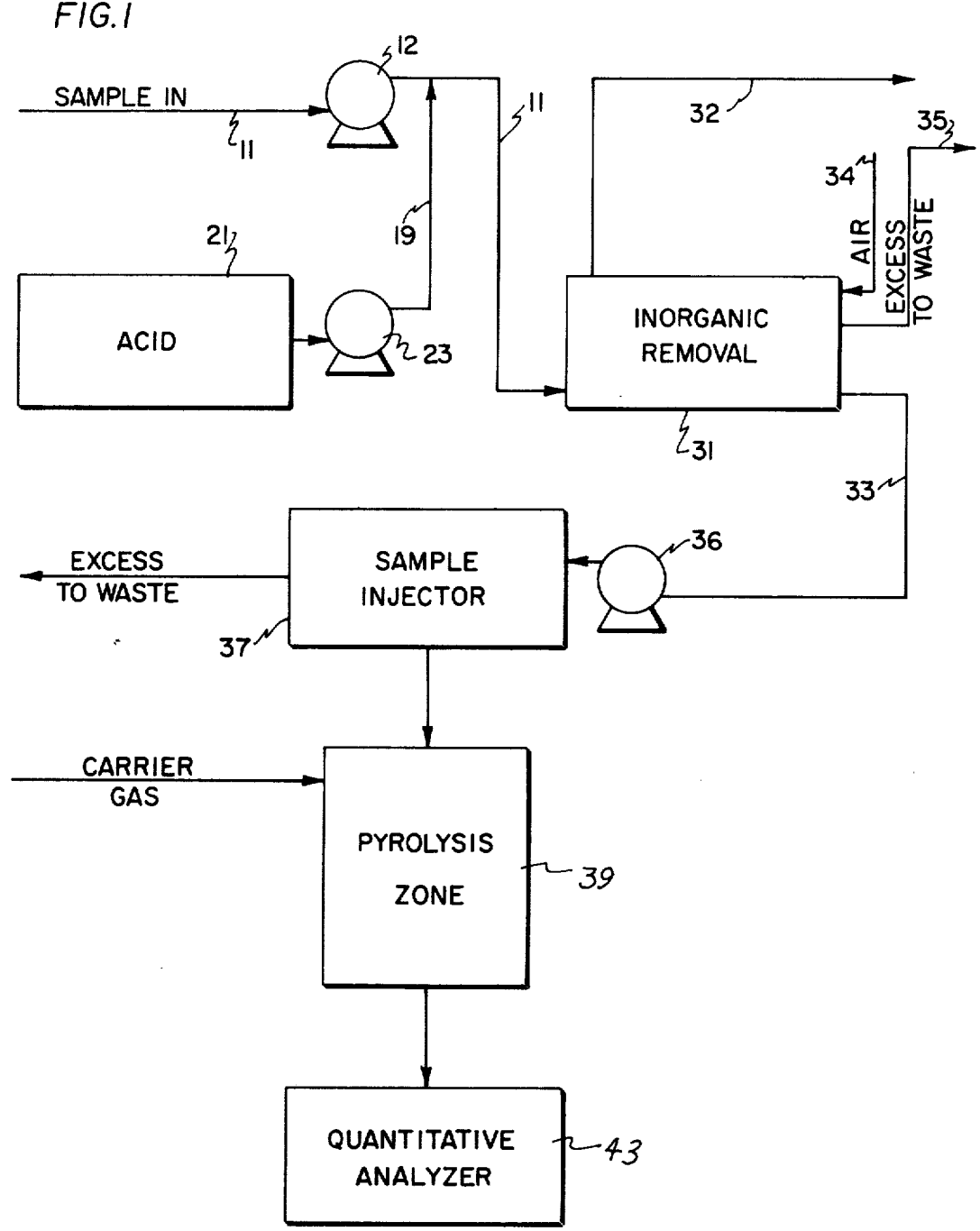
FIG. 1 is a schematic diagram of a system utilizing the invention.

Referring now to FIG. 1, an aqueous stream enters the analysis system via a conduit 11 and a pump 12. The aqueous influent can be a solution, brine, suspension or slurry, for example. Within the system the aqueous stream comes into confluence with acid that is carried by a conduit 19 from a reservoir 21. Upon addition of the acid to the influent, a reaction takes place analagous to the one described hereinbefore whereby carbon dioxide is formed from inorganic carbon compounds in the influent.

Downstream from the confluence, the conduit 11 connects into a sparging device 31 wherein carbon dioxide is purged from the aqueous phase and released as a gas through a conduit 32. As will be explained in more detail hereinafter, sparging gas is introduced into the sparger 31 via a conduit 34 and excess liquid is discharged via a conduit 35. Sparged liquid, which is free of carbon dioxide, passes from the sparger via conduit 33 and a pump 36 and then enters a sampling device 37 which functions to periodically draw a preselected aliquot volume of sample from the stream and inject the same into a conventional furnace 39. The unsampled portion of the sparged liquid is discharged.

The sampling device 37 can, for example, be a conventional slide-type valve or else a rotary sample injection valve of the type available from Dohrmann Division of Envirotech Corporation, Santa Clara, Calif. The furnace 39 can be a pyrolysis furnace or a fluidized bed reactor, for example.

From the furnace 39, the samples are carried in a stream of carrier gas into conventional analysis equipment 43 wherein a quantitative determination is made of the residual carbon content of the sample. Since only organic carbon compounds remain after sparging, the quantitative analysis of the stream measures the organic loading. The analysis equipment can, for example, be a conventional non-dispersive infrared detector or a conductometric detector where oxidative pyrolysis techniques are employed or a conventional flame ionization detector where reductive methods are practiced.

Figure 2:
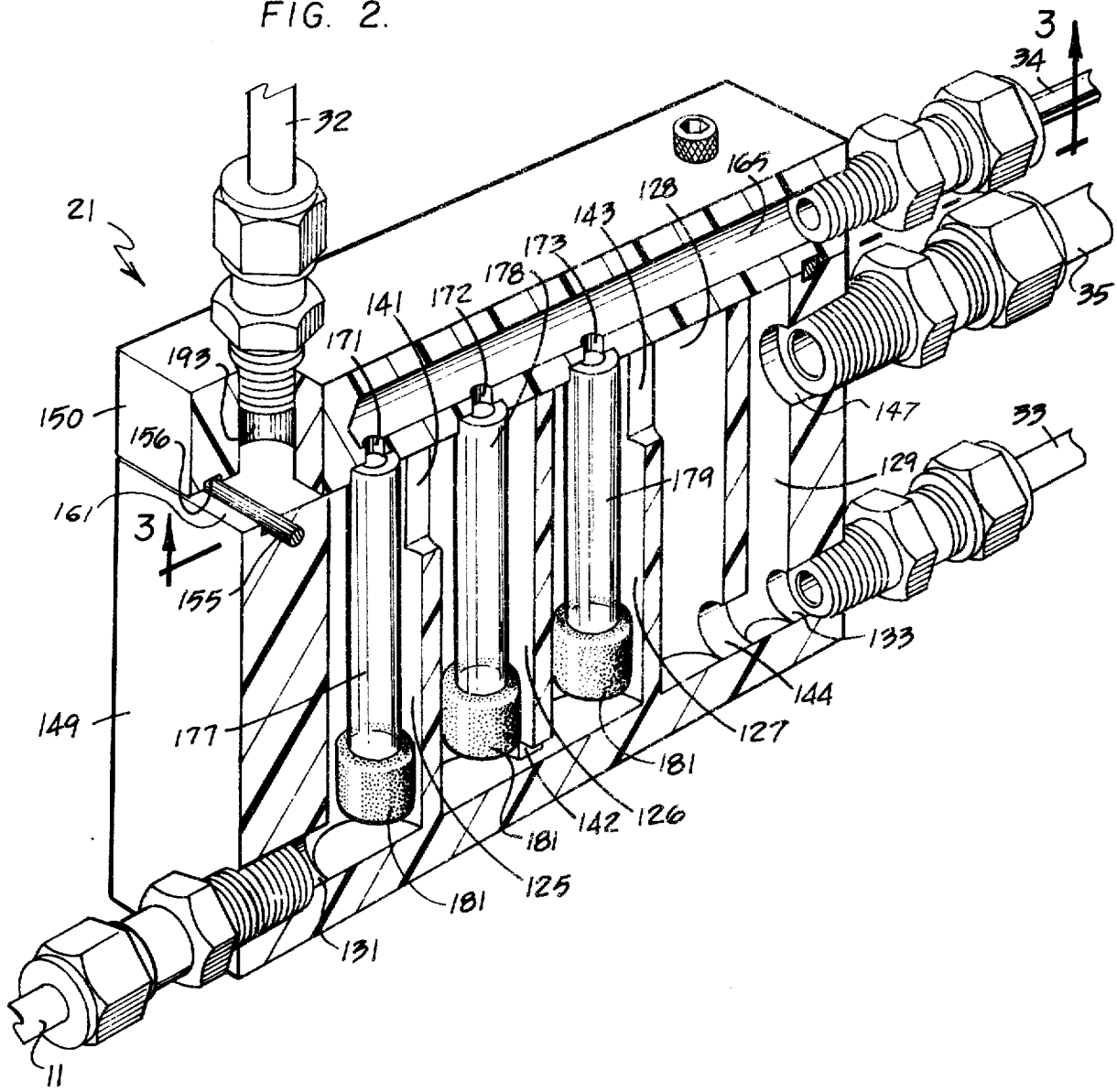
FIG. 2 is a pictorial view of a sparging device that is shown schematically in FIG. 1.

In the preferred embodiment shown in FIG. 2, the sparger has a non-foraminous body with a plurality of vertical cavities 125–129 formed side-by-side therethrough. The sparger body is preferably fabricated from two separate block-like sections 149 and 150 which are joined in face-to-face relationship one atop the other with a continuous seal or gasket member 155 located in matching grooves 156 formed in the mating faces 159 and 161. With such a two-part construction, the aforementioned cavities 125–129 can be drilled or otherwise formed directly in the lower body section before assemblage. Normally the body sections are formed from an inert material, such as fluorocarbon resin, to preclude chemical reaction with the acidified liquid.

The aforementioned conduit 11 that carries the acidified stream to the sparger is fitted into an inlet port 131 formed in direct communication with the bottom of the first vertical cavity 125. Adjacent ones of the vertical cavities 125–129 are connected by respective passageways 141–144 which are formed sequentially at the top and bottom ends of the cavities. Thus, for example, passageway 141 connects from the top of cavity 125 to cavity 126 and passageway 142 connects the lower end of cavity 126 with cavity 127. The last cavity 129 has an outlet port 147 formed at its upper end for connection to a discharge conduit 35 for maintaining a predetermined liquid level in the sparger and an outlet port 133 formed in its lower end for connection to the aforementioned sparged liquid outlet conduit 33. With the illustrated construction, liquid flows completely through a cavity before passing into the next in a vertically serpentine path through the sparger. In practice, all clearances within the sparger exceed about one-half centimeter so that particulates in the aqueous stream readily pass through the sparger without blockage.

The sparger 31 further includes a manifold chamber 165 that is formed through the upper body section 150 across the tops of the cavities 125–129. The manifold is connected at one end to the aforementioned conduit 34 that is in communication with a source of sparging gas such as compressed air, oxygen, nitrogen or the inert gases. Apertures 171–173 are formed through the sidewall of the manifold 165 in direct communication with the respective cavities 125–127. Downwardly-depending hollow dispersion tubes 177–179 are sealingly fitted into the respective apertures 171–178 in concentric relationship with the cavities. The ends of the dispersion tubes 177–179 adjacent the bottoms of the cavities are capped by fluid-pervious members 181, made from fused glass particles or the like. The capped dispersion tubes are commercially available items. With such an arrangement, air or oxygen readily passes from the manifold 165 into the dispersion tubes 171–173 and thence into the cavities 125–127 as very fine bubbles.

Figure 3:
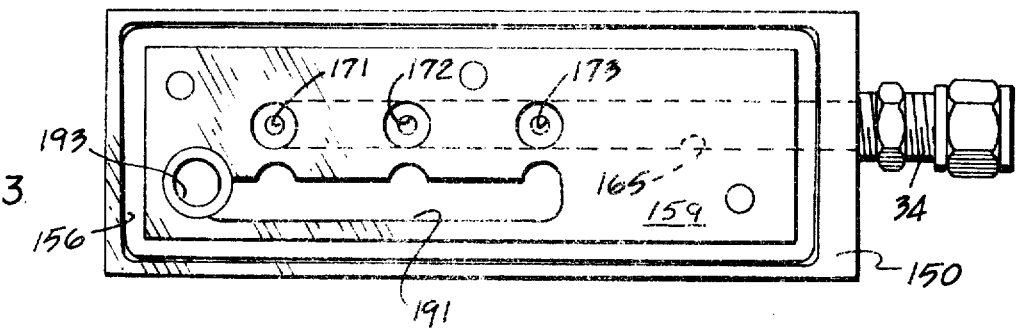
FIG. 3 is a sectional view of the device shown in FIG. 2 taken along the line 3—3 viewed in the direction of the arrows.

As best shown in FIG. 3, an open channel or groove 191 is formed in the mating face 159 of the upper body section 150 completely isolated from the first manifold 165 but in direct communication with the first three cavities 125–127 in the lower body section 149 about the peripheries of the dispersion tubes 177–179. The channel 191 functions as a vapor-collecting space as will be described later herein. A port 193 is formed in communication with the channel 191 and the aforementioned vent conduit 32 is sealingly secured thereinto.

The operation of the sparging device 21 will now be described. Initially, acidified sample enters the first cavity 125 via the port 131 and then passes successively up and down through the respective cavities 125–128. Concomitantly, sparging gas enters the manifold 165 and passes down through the hollow dispersion tubes 177–179 for introduction into the cavities 125–127 as fine bubbles. Carbon dioxide is evolved from the liquid in the cavities by absorption onto the gaseous bubbles of sparging gas, which bubbles rise and pass from the liquid into the channel 191 and thence to discharge via the port 193. By utilizing an excess of sparging gas to continuously sweep the vapor space formed by the channel 191, the carbon dioxide partial pressure is depressed which, in turn, encourages the vaporization of further carbon dioxide.

Cascading or employing three sparging cavities in series has been found to accomplish a dramatic increase in efficiency. For example, with one sparger the carbon-dioxide efficiency is on the order of 65% whereas with two sparging cavities in series, the efficiency of removal has been found to increase to about 95% and with three to 99.9%.

I claim:

1. A device for sparging carbon dioxide from an acidified aqueous stream for use in a system for quantitatively determining the organic carbon content of the stream comprising:
   a. a generally non-foraminous body having a first cavity, a last cavity and between them a plurality of cavities, each generally vertically extending and formed therethrough;
   b. an inlet port formed in said body in fluid-flow communication with said first cavity for admitting an acidified aqueous stream into the body;
   c. passageways connecting said cavities in series so that the aqueous stream travels the length of each of said cavities before passing into the next;
   d. an outlet port formed in said body in fluid-flow communication with the lower end of said last cavity for discharging the sparged aqueous stream from said body;
   e. a manifold formed in said body and communicating with means to supply sparging gas into said manifold;
   f. sparging gas dispersion means mounted in at least two of said cavities for dispersing fine bubbles of sparging gas into the aqueous stream in said cavities, said gas dispersion means comprising hollow tubes which carry sparging gas from said manifold into said cavities;
   g. gas collection and discharge means in fluid flow communication with said cavities for continuously discharging sparging gas and carbon dioxide which has evolved from the aqueous stream passing through the cavities; and
   h. means to maintain a predetermined liquid level within said cavities, said means including a liquid outlet port formed in said body in fluid flow communication with the upper end of said last cavity.

2. A device according to claim 1 including fluid-pervious members which cap the ends of said tubes within said cavities.

* * * * *